United States Patent [19]

Crowley et al.

[11] Patent Number: 4,586,947
[45] Date of Patent: May 6, 1986

[54] AZOLYL-HYDROXY ALKANOLS HAVING FUNGICIDAL AND PLANT GROWTH REGULATING PROPERTIES

[75] Inventors: Patrick J. Crowley, Crowthorne; John C. Williams, Bracknell, both of England

[73] Assignee: Imperial Chemical Industries PLC, London, England

[21] Appl. No.: 451,763

[22] Filed: Dec. 21, 1982

[30] Foreign Application Priority Data

Feb. 3, 1982 [GB] United Kingdom ............... 8203097

[51] Int. Cl.$^4$ ................ A01N 43/50; A01N 43/653; C07D 233/60; C07D 249/08
[52] U.S. Cl. ........................................ 71/76; 71/92; 514/184; 514/383; 514/399; 548/101; 548/262; 548/341
[58] Field of Search ............... 548/101, 262, 341; 424/269, 273 R, 245

[56] References Cited

U.S. PATENT DOCUMENTS

| | | | |
|---|---|---|---|
| 3,993,765 | 11/1976 | Buchel et al. | 424/269 |
| 4,130,409 | 12/1978 | Shephard et al. | 71/76 |
| 4,154,842 | 5/1979 | Kramer et al. | 548/262 |
| 4,217,129 | 8/1980 | Shephard et al. | 548/341 |
| 4,269,845 | 5/1981 | Shephard et al. | 548/341 |

FOREIGN PATENT DOCUMENTS

| | | | |
|---|---|---|---|
| 0015756 | 7/1980 | European Pat. Off. | 548/262 |
| 0052424 | 5/1982 | European Pat. Off. | 548/262 |
| 0061835 | 10/1982 | European Pat. Off. | 548/262 |
| 2246548 | 5/1975 | France | 548/341 |

*Primary Examiner*—Alton D. Rollins
*Attorney, Agent, or Firm*—Cushman, Darby & Cushman

[57] ABSTRACT

Compounds having the general formula (I):

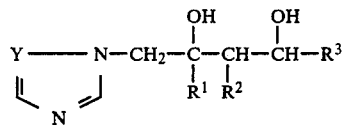

wherein Y is —CH= or =N—, $R^1$ is alkyl, cycloalkyl optionally substituted phenyl and $R^2$ and $R^3$, which may be the same or different, are hydrogen, alkyl, cycloalkyl, (e.g. cyclopropyl, cyclopentyl or cyclohexyl) optionally substituted phenyl or optionally substituted benzyl, or together form an alkylene bridging group; and acid addition salts; metal complexes; ether and ester derivatives of the hydroxy groups; and stereoisomers thereof. These compounds have fungicidal and plant growth regulating properties.

3 Claims, No Drawings

AZOLYL-HYDROXY ALKANOLS HAVING FUNGICIDAL AND PLANT GROWTH REGULATING PROPERTIES

This invention relates to triazole compounds useful as fungicides, to a process for preparing them, to fungicidal compositions containing them, and to a method of combating fungal infections in plants using them.

The triazole compounds have the general formula (I):

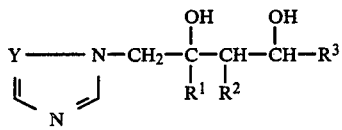

wherein Y is —CH= or =N—, $R^1$ is alkyl, cycloalkyl or optionally substituted phenyl and $R^2$ and $R^3$, which may be the same or diffferent, are hydrogen, alkyl, cycloalkyl, (e.g. cyclopropyl, cyclopentyl or cyclohexyl), optionally substituted phenyl or optionally substituted benzyl, or together form an alkylene ring; and the invention includes acid addition salts; metal complexes; ether and ester derivatives of the hydroxy groups and stereoisomers thereof.

The compounds of the invention can contain chiral centres. Such compounds are generally obtained in the form of racemic mixtures. However, these and other mixtures can be separated into the individual isomers by methods known in the art.

The alkyl groups can be a straight or branched chain groups having 1 to 6, e.g. 1 to 4, carbon atoms; examples are methyl, ethyl, propyl (n- or iso-propyl) and butyl (n-, sec-, iso- or t-butyl).

Examples of suitable substituents for the phenyl and for the phenyl moiety of the benzyl are halogen, alkyl, alkoxy, nitro and phenyl. The alkyl moiety (i.e. the α-carbon) of the benzyl can be substituted with, for example, one alkyl (e.g. methyl or ethyl). Suitably the phenyl and benzyl are unsubstituted or substituted with 1, 2 or 3 ring substituents as defined above. Examples of these groups are phenyl, benzyl α-methylbenzyl, 2-, 3- or 4-chloro-phenyl, 2,4- or 2,6-dichlorophenyl, 2-, 3- or 4-, fluoro-phenyl, 2-, 3- or 4-bromophenyl, 2-, 3- or 4-methoxyphenyl, 2,4-dimethoxyphenyl, 2-, 3- or 4-ethoxyphenyl, 2-, 3- or 4-nitrophenyl, 2-, 3- or 4- methylphenyl, 2-, 3- or 4-trifluoromethylphenyl, 2-chloro-4-methylphenyl, 2-chloro-4-methoxyphenyl, 2-chloro-4-cyano-phenyl, and 4-phenylphenyl (4-biphenylyl), and the corresponding ring substituted benzyl and α-methylbenzyl groups.

In a further aspect, therefore, the invention provides a compound of formula (I) above, or a stereoisomer thereof, wherein $R^1$ is a straight or branched chain alkyl group having from 1 to 6 carbon atoms or is phenyl optionally substituted with halogen, alkyl, alkoxy, nitro, phenyl or phenoxy; $R^2$ and $R^3$ are together an alkylene bridging group, or each represents hydrogen, straight or branched chain alkyl groups having from 1 to 6 carbon atoms, phenyl or benzyl each optionally substituted with halogen, alkyl, alkoxy, nitro, phenyl or phenoxy, the alkyl moiety of the benzyl being optionally substituted with alkyl; and Y is =CH— or =N—.

In a preferred aspect the invention provides a compound of formula (I) above, or a stereoisomer thereof, wherein $R^1$ is an alkyl group containing from 1 to 4 carbon atoms or is halophenyl, $R^2$ is hydrogen or methyl; $R^3$ is hydrogen or an alkyl group containing from 1 to 4 carbon atoms; and Y is =N— or =CH—.

The ester and ether derivatives of the hydroxy groups are suitably alkanoates (e.g. acetates) and alkyl (e.g. methyl or ethyl), aryl (e.g. phenyl) or aralkyl (e.g. benzyl) groups.

The salts can be salts with inorganic or organic acids e.g. hydrochloric, nitric, sulphuric, acetic, 4-toluenesulphonic or oxalic acid.

Suitably the metal complex is one including, as the metal, copper, zinc, manganese or iron. It preferably has the general formula:

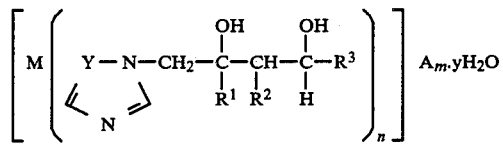

wherein Y, $R^1$, $R^2$ and $R^3$ are as defined above, M is a metal, A is an anion (e.g. a chloride, bromide, iodide, nitrate, sulphate or phosphate anion), n is 2 or 4, y is O or an integer of 1 to 12, and m is an integer consistent with valency.

Examples of the compounds of the invention are shown in Table 1. These conform to formula I.

TABLE 1

| COMPOUND NO | $R^1$ | $R^2$ | $R^3$ | Y | MELTING POINT (°C.) |
|---|---|---|---|---|---|
| 1 | 2,4-dichlorophenyl | H | ethyl | =N— | 58–61 |
| 2 | 4-chlorophenyl | H | tertiary butyl | =N— | |
| 3 | 4-fluorophenyl | H | tertiary butyl | =N— | |
| 4 | 2,4-dichlorophenyl | *—CH$_2$—CH$_2$—CH$_2$— | | =N— | 185–187 |
| 5 | tertiary butyl | H | tertiary butyl | =N— | |
| 6 | 2,4-dichlorophenyl | H | tertiary butyl | =N— | 124–126 |
| 7 | 2,4-dichlorophenyl | H | normal butyl | =N— | |
| 8 | 2,4-dichlorophenyl | H | tertiary butyl | =CH— | |
| 9 | 2,4-dichlorophenyl | CH$_3$ | tertiary butyl | =N— | |
| 10 | 2,4-dichlorophenyl | CH$_3$ | tertiary butyl | =CH— | |
| 11 | 4-chlorophenyl | CH$_3$ | tertiary butyl | =N— | |
| 12 | 4-chlorophenyl | CH$_3$ | tertiary butyl | =CH— | |
| 13 | 4-(4-chloro-phenyl)phenyl | H | tertiary butyl | =N— | |
| 14 | 4-(4-chloro-phenyl)phenyl | H | tertiary butyl | =CH— | |
| 15 | 2,4-dichlorophenyl | CH$_3$ | iso-propyl | =N— | 58–60 |
| 16 | 2,4-dichlorophenyl | CH$_3$ | ethyl | =N— | 73–76 |
| 17 | 2,4-dichlorophenyl | H | n-propyl | =N— | Oil |
| 18 | 2,4-dichlorophenyl | H | H | =N— | Oil |

TABLE 1-continued

| COMPOUND NO | R¹ | R² | R³ | Y | MELTING POINT (°C.) |
|---|---|---|---|---|---|
| 19 | 2,4-dichlorophenyl | H | iso-propyl | =N— | 170-173 |

*R² and R³ together form an alkylene bridge
°ie. R² and R³ together form a bridging group Compounds of general formula (I) may be produced by reduction of compounds of general formula (II), using standard reducing agents, particularly metal hydrides such as sodium borohydride and lithium aluminium hydride

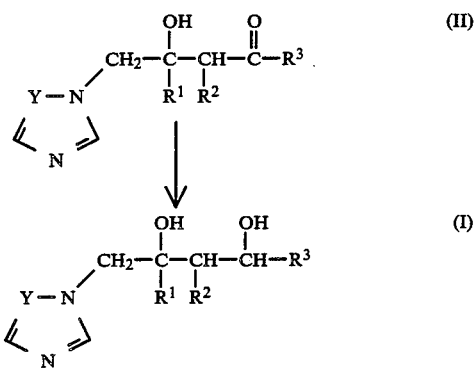

the former in alcoholic solvents or water, the latter in ether or THF (tetrahydrofuran), usually at temperatures 0°–50°. The product can be isolated by pouring the deaction mixture into water and recrystallising the solid, or extracting with a solvent in the usual way.

The compounds of general formula (I) may be produced by reacting a compound of general formula (II) with the enolate anion (IV), generated by treatment of (III) with a strong base such as lithium diisopropylamide.

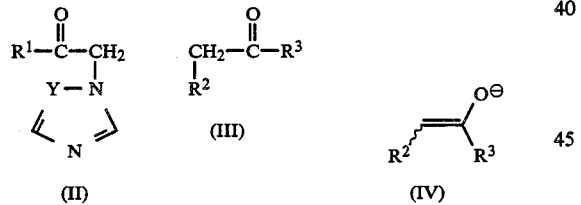

The compounds of general formula (II) and (III) may be made by methods set out in the literature.

Suitably the compounds of general formula (II) are reacted with the enolate anion of (IV) in a solvent such as THF at low temperature (−78° to −40° C.). The product can be isolated by pouring the reaction mixture into water and recrystallising the solid formed from a convenient solvent.

The salts and metal complex of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: *Fusarium* spp., *Septoria* spp., *Tilletia* spp. (i.e. bunt, a seed borne disease of wheat), *Ustilago* spp., *Helminthosporium* spp. on cereals, *Rhizoctonia solani* on cotton and *Corticuium sasakii* on rice.

The compounds can move acropetally in the plant tissue. Moreover, the compounds can be volatile enough to be active in the vapour phase aginst fungi on the plant.

The compounds are also useful for the treatment of candidiasis and human dermatophyte infections.

The compounds may be used as such for fungicidal purposes but are more conveniently formulated into compositions for such usage. The invention thus provides also a fungicidal composition comprising a compound of general formula (I) or a salt or complex thereof as hereinbefore defined, and a carrier or diluent.

The invention also provides a method of combating fungal diseases in a plant, which method comprises applying to the plant, to seed of the plant, or to the locus of the plant or seed, a compound, or a salt or complex thereof, as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, di-acetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2- butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal fungal diseases.

Suitable insecticides are pirimor, croneton, dimethoate, metasystox and formothion.

Examples of suitable plant growth regulating compounds are the gibberellins (e.g. GA3, GA4 or GA7), the auxins (e.g. indoleacetic acid, indolebutyric acid, naphthoxyacetic acid or naphthylacetic acid), the cytokinins (e.g. kinetin, diphenylurea, benzimidazole, benzyl-adenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat or chlorphonium), ethephon, carbetamide, methyl-3,6-dichloranisate, daminozide, asulam, abscissic acid, isopyrimol, 1-(4-chlorophenyl)-4,6-dimethyl-2-oxo-1,2-dihydropyridine-3-carboxylic acid, hydroxybenzonitriles (e.g. difenzoquat, benzoylprop-ethyl 3,6-dichloropicolinic acid.

The following Examples illustrate the invention; the temperatures are given in degrees Centigrade (°C).

EXAMPLE 1

This Example illustrates the preparation of the intermediate compound having the chemical structure:

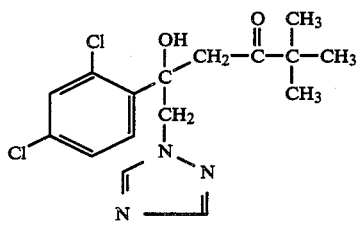

n-Butyl lithium (6.5 ml of a 1.6 m solution in hexane) was slowly added dropwise to diisopropylamine (1.05 g) stirred in dry THF*(60 ml) at −20° C. under argon. After stirring for 30 minutes, p:nacolone (1.0 g) in dry THF (tetrahydrofuran) (10 ml) was slowly added dropwise to the solution cooled to −40° C. and after completion of the addition the reaction mixture was stirred at −40° for 30 minutes. 2,4-Dichlorophenacyltriazole (2.0 g) in dry THF (30 ml) was then slowly added in dropwise over 10 minutes and the mixture stirred at −40° for 30 minutes and then warmed to 5° over 2 hr. The reaction was then carefully quenched with water, and extracted with ether and the ethereal extract dried over magnesium sulphate. Evaporation of the solvent yielded a viscous oil which was chromatographed on silica gel, eluting with ethyl acetate. The product was obtained as an oil (0.60 g).
* THF=tetrahydrofuran NMR (CDCl3)δ: 1.00(s,9H), 2.56(d,1H), 4.10(d,1H), 4.52(d,1H), 4.92(d,1H), 5.95(s,1H), 7.14–7.40(m,2H), 7.68(d,1H), 7.78(s,1H), 8.15(s,1H).

IR (liquid film) 3380, 1690 cm−1.

EXAMPLE 2

The preparation of:

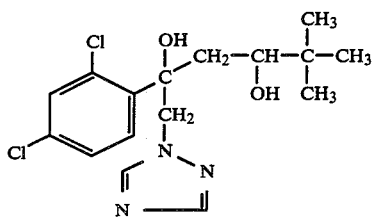

(Compound No 6 of Table 1)

The ketone prepared according to Stage 1 above (1.0g) was stirred at 10° C. in methanol (10 ml). Sodium borohydride (0.18 g) was added portionwise maintaining the temperature at about 10° C. After completion of the addition the mixture was stirred for 1 hour at room temperature. Saturated ammonium chloride solution was added and the mixture extracted with ether. The extract was washed with water, dried and evaporated to give a glass, which cyrstallised on standing with petrol/ether, to give a white solid mpt 124°-6° (0.50 g).

NMR (CDCl3)δ: 1.0(s,9H), 1.50–2.05(m,2H), 3.50–4.00(m,1H), 4.70–5.00(m,1H), 5.20–5.60 (m,1H), 7.2–8.40 (envelope, 5H).

IR (nujol) 3400–2600 cm−1.

EXAMPLE 2A

Stage 1

This stage illustrates the preparation of the compound:

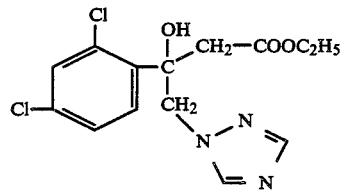

To Lithium bis-(trimethylsilyl)amide (40 ml of a 1 M solution in hexane), stirring in dry THF (100 ml) at −78° (internal temp) under argon, was added ethyl acetate (3.8 gm) over 15 minutes, maintaining the temperature at −78°. The clear slightly yellow solution was stirred for 10 minutes at the same temperature. The 2,4-dichlorophenacyltriazole (10.4 g) in dry THF (40 ml) was added dropwise over 1 hour, again maintaining the temperature at −78°, and then the solution was stirred at that temperature for 15 minutes after completion of the addition.

The reaction was quenched at −78° by water and the product extracted with ether, and the ethereal solution washed with water and then dried.

The ether was evaporated leaving an oil which solidified on scratching in the presence of a little ether. Yield=5.3 g. The product had identical spectral data to previously prepared samples.

NMR (CDCl3)δ1.16 (t,3H), 2,82 (d,1H), 3.64 (d,1H) 4.10 (q,2H), 4.88 (q,2H), 5.40 (s,1H) 7.30 (dd,1H), 7.46 (d,1H), 7.76 (d,1H) 7.92 (s,1H), 22 (s,1H).

IR (nujol) 1730 cm−1.

Stage 2

This stage illustrates the preparation of the compound:

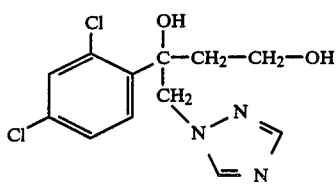

(Compound No. 18 of Table I)

To the dry ester prepared above (1.0 g) in dry toluene (5 ml), stirring at room temperature, was added *Red-Al (1.5 ml) dropwise. An immediate reaction set in, and after completion of the addition the mixture was stirred for a further 15 minutes. It was then quenched into aqueous sodium hydroxide and extracted with ether. The ether was dried and evaporated to yield an oil (0.45 gm).
* Red-Al is sodium bis (2-methoxyethoxy)aluminium hydride.

NMR (CDCl$_3$)δ1.70–2.20 (m,1H), 2.72 (bd,1H), 3.30–3.90 (m,2H), 4.76 (s,2H), 5.76 )s,1H), 7.10–7.50 (m,2H), 7.76 (s,1H), 7.81 (s,1H), 8.16 (s,1H).

IR (liquid film) 3400–3100 cm$^{-1}$.

More detailed examination of the NMR spectrum showed that the diol was an approximately 1:1 mixture of diasteroisomers.

EXAMPLE 3

An emulsifiable concentrate was made up by mixing the ingredients, and stirring the mixture until all the constituents were dissolved.

| Compound No 6 of Table 1 | 10% |
| --- | --- |
| Ethylene dichloride | 40% |
| Calcium dodecylbenzenesulphate | 5% |
| "Lubrol" L | 10% |
| "Aromasol" H | 35% |

EXAMPLE 4

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100 to obtain the desired size of grains.

| Compound of Example 1 | 50% |
| --- | --- |
| "Dispersol" T | 25% |
| "Lubrol" APN5 | 1.5% |
| Sodium acetate | 23.5% |

EXAMPLE 5

The ingredients were all ground together to produce a powder formulation readily dispersible in liquids.

| Compound of Example 1 | 45% |
| --- | --- |
| "Dispersol" T | 5% |
| "Lissapol" NX | 0.5% |
| "Cellofas" B600 | 2% |
| Sodium acetate | 47.5% |

EXAMPLE 6

The active ingredient was dissolved in a solvent and the resultant liquid was sprayed on to the granules of China clay. The solvent was then allowed to evaporate to produce a granular composition.

| Compound of Example 1 | 5% |
| --- | --- |
| China clay granules | 95% |

EXAMPLE 7

A composition suitable for use as a seed dressing was prepared by mixing the three ingredients.

| Compound of Example 1 | 50% |
| --- | --- |
| Mineral oil | 2% |
| China clay | 48% |

EXAMPLE 8

A dusting powder was prepared by mixing the active ingredient with talc.

| Compound of Example 1 | 5% |
| --- | --- |
| Talc | 95% |

EXAMPLE 9

A col formulation was prepared by ball-milling the constituents set out below and then forming an aqueous suspension of the ground mixture with water.

| Compound of Example 1 | 40% |
| --- | --- |
| "Dispersol" T | 10% |
| "Lubrol" APN5 | 1% |
| Water | |

EXAMPLE 10

A dispersible powder formulation was made by mixing together the ingredients set out below and then grinding the mixture until all were thoroughly mixed.

| Compound of Example 1 | 25% |
| --- | --- |
| "Aerosol" OT/B | 2% |
| "Dispersol" A.C. | 5% |
| China clay | 28% |
| Silica | 40% |

EXAMPLE 11

This Example illustrates the preparation of a dispersible powder formulation. The ingredients were mixed and the mixture then ground in a comminution mill.

| Compound of Example 1 | 25% |
| --- | --- |
| "Perminal" BX | 1% |
| "Dispersol" T | 5% |
| Polyvinylpyrrolidone | 10% |
| Silica | 25% |
| China clay | 34% |

EXAMPLE 12

The ingredients set out below were formulated into a dispersible powder by mixing then grinding the ingredients.

| Compound of Example 1 | 25% |
|---|---|
| "Aerosol" OT/B | 2% |
| "Dispersol" A | 5% |
| China clay | 68% |

In Examples 3 to 12 the proportions of the ingredients given are by weight.

There now follows an explanation of the compositions or substances represented by the various Trade Marks and Trade Names mentioned above.

| LUBROL L: | a condensate of nonyl phenol (1 mole) with ethylene oxide (13 moles). |
|---|---|
| AROMASOL H: | a solvent mixture of alkylbenzenes. |
| DISPERSOL T & AC: | a mixture of sodium sulphate and a condensate of formaldehyde with sodium naphthalene sulphonate. |
| LUBROL APN5: | a condensate of nonyl phenol (1 mole) with naphthalene oxide (5.5 moles). |
| CELLOFAS B600: | a sodium carboxymethyl cellulose thickener. |
| LISSAPOL NX: | a condensate of nonyl phenol (1 mole) with ethylene oxide (8 moles). |
| AEROSOL OT/B: | dioctyl sodium sulphosuccinate. |
| PERMINAL BX: | a sodium alkyl naphthalene sulphonate. |

EXAMPLE 13

The compounds were treated against a range of mainly foliar fungal diseases of plants. The techniques used were as follows:

For all tests other than that against *Botrytis cintnea* the plants were grown in John Innes Potting Compost (No. 1 or 2) in 4 cm diameter minipots. A layer of fine sand was placed at the bottom of the pots containing the dicotyledonous plants to facilitate uptake of test compounds by the roots. The test compounds were formulated either by bead milling with aqueous Dispersol T or as a solution in acetone or acetone/ethanol which was diluted to the required concentration immediately before use. For the foliage diseases, solutions and suspensions (100 ppm ai.) were sprayed on the foliage and applied to the roots of the plant via the soil. For the test against *Botrytis cinera*, grape berries were sprayed with the test compounds. The sprays were applied to maximum retention and the root drenches to a final concentration equivalent to approximately 40 ppm ai./dry soil. Tween 20, to give a final concentration of 0.05%, was added when the sprays were applied to cereals. (ai. means "active ingredient").

Most were protectant tests where the compound was applied to the soil and roots and to the foliage one or two days before the plant was innoculated with the pathogen. However, in the case of the tests against *Erisyphe graminis hordei* and *Botrytis cinera*, the treatment was eradicative and the compounds were applied one day after inoculation.

Inoculation of the grape berrries in the *Botrytis cinerea* test was achieved by slitting fruits twice and then immersing them in a spore suspension of the pathogen. The remaining foliar pathogens were applied by spray as spore suspensions onto the leaves of the test plants. After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:

4=no disease
3=trace to 5% of disease on untreated plants
2=6-25% of disease on untreated plants
1=26-59% of disease on untreated plants
0=60-100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMAPARA VITICOLA (VINE) | PHYTOPHTHORA INFESTANS (TOMATO) | BOTRYTIS CINEREA (GRAPE) | CERCOSPORA ARACHIDICOLA (PEANUT) | VENTURIA INEQUALIS (APPLE) |
|---|---|---|---|---|---|---|---|---|
| 1 | 4 | 4 | 4 | 0 | — | 0 | 4 | 4 |
| 4 | 4 | 4 | 4 | 2 | — | 0 | 4 | 4 |
| 6 | 4 | 4 | — | 2 | — | 0 | 4 | 4 |
| 15 | 4 | 4 | 4 | 1 | — | 0 | 4 | 4 |
| 16 | 4 | 4 | 4 | 0 | — | 0 | 4 | 4 |
| 17 | 4 | 4 | 3 | 0 | — | 0 | 3 | 4 |
| 18 | 3 | 4 | 3 | 0 | — | 0 | 4 | 4 |
| 19 | 4 | 4 | 3 | 0 | — | 2 | 4 | 4 |

We claim:

1. A compound having the formula (I):

$$Y\underset{N}{\underset{\parallel}{\overset{}{\rule{0pt}{0pt}}}}N-CH_2-\underset{R^1}{\overset{OH}{\underset{\mid}{C}}}-\underset{R^2}{\overset{}{\underset{\mid}{CH}}}-\overset{OH}{\underset{\mid}{CH}}-R^3 \quad (I)$$

wherein Y is =N—; $R^1$ is 4-chlorophenyl or 2,4-dichlorophenyl; $R^2$ is methyl or ethyl and $R^3$ is aklyl having from 1 to 4 carbon atoms, and acid addition salts, metal complexes, lower alkanoate, lower alkyl or benzyl derivatives of the hydroxy group and stereoisomers thereof.

2. A fungicidal, or plant growth regulating composition comprising an effective amount of a compound of general formula (I) as defined in claim 1 and a carrier or diluent.

3. A method of combating fungal diseases in a plant, which method comprises applying to the plant, to seed of the plant, or to the locus of the plant or seed, a compound, according to claim 1.

* * * * *